(12) United States Patent
Jordan et al.

(10) Patent No.: US 9,889,035 B2
(45) Date of Patent: Feb. 13, 2018

(54) ORTHOSIS LOADING MANAGEMENT

(71) Applicant: Camp Scandinavia AB, Helsingborg (SE)

(72) Inventors: Heinrich Jordan, Ystad (SE); Olof Eklund, Helsingborg (SE); Gunilla Ström, Helsingborg (SE)

(73) Assignee: Camp Scandinavia AB, Helsingborg (SE)

( * ) Notice: Subject to any disclaimer, the term of this patent is extended or adjusted under 35 U.S.C. 154(b) by 0 days.

(21) Appl. No.: 15/093,993

(22) Filed: Apr. 8, 2016

(65) Prior Publication Data

US 2016/0220407 A1    Aug. 4, 2016

Related U.S. Application Data

(63) Continuation of application No. PCT/IB2014/002821, filed on Oct. 10, 2014.
(Continued)

(51) Int. Cl.
*A61F 5/01* (2006.01)
*A61F 5/058* (2006.01)

(52) U.S. Cl.
CPC .......... *A61F 5/0113* (2013.01); *A61F 5/0111* (2013.01); *A61F 5/0585* (2013.01)

(58) Field of Classification Search
CPC .. A61F 5/00; A61F 5/01; A61F 5/0102; A61F 5/0104; A61F 5/0111;
(Continued)

(56) References Cited

U.S. PATENT DOCUMENTS 5,456,658 A   10/1995   Duback et al.
5,624,386 A    4/1997   Tailor et al.
(Continued)

FOREIGN PATENT DOCUMENTS

EP   0934749 A1    8/1999
EP   2524674 A1   11/2012
(Continued)

OTHER PUBLICATIONS

International Search Report and Written Opinion for PCT/IB2014/002821, dated Jul. 30, 2015, 16 pages.

*Primary Examiner* — Keri J Nelson
(74) *Attorney, Agent, or Firm* — Grasso PLLC

(57) ABSTRACT

Laminate orthoses, preferably fiber-reinforced laminate orthoses, and preferably ankle-foot orthoses, are described. The shape, relative orientation, and positioning of layers comprising the orthoses may be configured and assembled in embodiments to manage the distribution of external static and dynamic loads through and within the orthosis. Peak stresses and strains developed in the orthosis from external static or dynamic loading may be managed such that they may be greater in certain areas and lesser in other areas. Layers of material comprising an orthosis may have unique and/or nonuniform shapes with cutouts, nonuniform or ply drop offs, and tapering. These irregular configurations may serve to focus, increase, decrease, or otherwise manage internal stresses developed from external static and dynamic loading at various target areas of an orthosis.

22 Claims, 9 Drawing Sheets

Related U.S. Application Data

(60) Provisional application No. 61/890,294, filed on Oct. 13, 2013.

(58) Field of Classification Search
CPC .. A61F 5/0113; A61F 5/04; A61F 5/05; A61F 5/058; A61F 5/05825; A61F 5/05841; A61F 5/0585
USPC .......................................... 602/5, 23, 27–29
See application file for complete search history.

(56) References Cited

U.S. PATENT DOCUMENTS

| | | | |
|---|---|---|---|
| 5,766,724 | A | 6/1998 | Tailor et al. |
| 5,897,515 | A | 4/1999 | Willner et al. |
| 6,146,344 | A | 11/2000 | Bader |
| 6,887,213 | B2 * | 5/2005 | Smits .................... A61F 5/0111 602/23 |
| 7,270,644 | B2 | 9/2007 | Ingimundarson |
| 7,625,349 | B2 | 12/2009 | Bleau |
| 7,819,832 | B2 | 10/2010 | Balzer |
| 8,397,403 | B2 | 3/2013 | Guenther |
| 8,480,604 | B2 | 7/2013 | Messer |
| 2004/0154192 | A1 | 8/2004 | Bengtsson et al. |

FOREIGN PATENT DOCUMENTS

| | | |
|---|---|---|
| WO | 9531950 | 11/1995 |
| WO | 2008036034 A1 | 3/2008 |

* cited by examiner

ORTHOSIS LOADING MANAGEMENT

RELATED CASES

This application is a continuation of PCT application PCT/IB2014/002821 filed on Oct. 10, 2014 and entitled Orthosis Loading Management. The '821 PCT application claims priority to U.S. provisional application No. 61/890,294, which was filed on Oct. 13, 2013 and is entitled Orthosis Loading Management. The entirety of the '294 provisional application and the '821 PCT application are incorporated by reference into this application.

TECHNICAL FIELD

Composite orthoses and related systems, processes, and articles of manufacture are provided. More specifically, composite material layer configuration and design are provided for composite orthoses, as well as for processes and systems involving composite orthoses.

BACKGROUND

Orthoses are often considered to be devices, external of the body, that serve to or are used to alter, modify, or support, structural and/or functional characteristics of the body's skeletal or neuromuscular systems. For example, an orthosis may be used to retard the progression of scoliosis or may be used to assist a person, such as a person suffering with foot nerve damage, with walking. Orthoses can provide confinement and support in static situations, such as in retarding further spinal curving of a patient with scoliosis, and in dynamic situations, such as with supporting and influencing gait of a patient suffering from drop foot. An orthosis may also immobilize, limit, steer, guide, or dictate the position or range of movement of a body extremity, a body joint, or a body area. Orthoses may be used for treatment, improved lifestyle, improved comfort, and for other reasons as well.

In certain orthoses, the weight of the wearer's body may be transferred through the orthosis; and certain orthoses may be used for restorative effects during rehabilitation. Ankle Foot Orthoses (AFOs), including the subset of Knee Ankle Foot Orthoses (KAFOs), are examples of orthoses whose names identify the body parts that they are designed to supplement, restrict, guide, support or otherwise assist.

An orthotist may classify an orthosis as being a static orthosis or a functional orthosis. For example, a static orthosis may be used to stabilize a joint and surrounding soft tissue after surgery, hence it is used as an immobilization device. A functional orthosis, on the other hand, can be used to guide a joint to regain or maintain the normal joint function and/or to support a joint and/or surrounding soft tissue to ameliorate neuromuscular weakness. Orthoses used to guide or support a user through an activity or movement, such as normal gait, can be equipped with external joints, often called articulated orthoses, such as articulated Ankle Foot Orthoses.

BRIEF DESCRIPTION

Fiber-reinforced laminate orthoses are provided in embodiments. The shape, relative orientation, and positioning of layers comprising the orthoses may be configured and assembled in embodiments to manage the distribution of external static and dynamic loads through and within the orthosis. The shape, including their geometrical outline, thickness, and other external dimensions; relative orientation; and positioning of the layers or lamina may also be configured and assembled to manage the amount of loading stresses and loading strains developed in various areas of the orthosis. Likewise, fiber orientation in both unidirectional composite layers and bidirectional composite layers may also be considered in embodiments and may play a role in orthosis performance in embodiments.

In embodiments, peak stresses and strains developed in the orthosis from external static or dynamic loading may be managed such that they may occur in stress concentration zones or strain concentration zones. Likewise, damage initiation and damage propagation of the composite may also be considered for and during design and analysis. Still further, the shape, relative orientation, and positioning of the layers in an orthosis, as well as layer composition and manufacture of the orthosis, fiber orientation of layers, and layer thickness, may each be configured and assembled to manage the durability, toughness, and tolerable stresses for the composite lamina and laminate in embodiments. These properties and any modifications may also consider tolerable stresses for the composite lamina and laminate, for damage initiation, and for damage propagation. In embodiments, the composite material layers may be reinforced by various reinforcing fibers including carbon fiber, glass fiber, and aramid fiber, among others.

In embodiments, layers of material comprising an orthosis may have unique and/or nonuniform shapes with cutouts, nonuniform or ply drop offs, and tapering. These irregular configurations may serve to focus, increase, decrease, or otherwise manage internal stresses developed from external static and dynamic loading at various target areas of an orthosis. The global loading of an orthosis, e.g., torsional, tensile, and compressive loads, cause stresses in the material that may be managed in embodiments. These stresses, acting on the lamina level and being managed in embodiments, may include interlaminar and in-plane shear stresses, as well as compressive and tensile stresses.

In embodiments, movements that mimic joint movements of the wearer can be established by utilizing the mechanical properties of certain materials, and these orthoses are often referred to as dynamic orthoses, such as dynamic Ankle Foot Orthoses (AFOs).

DETAILED DESCRIPTION

Figure 1:
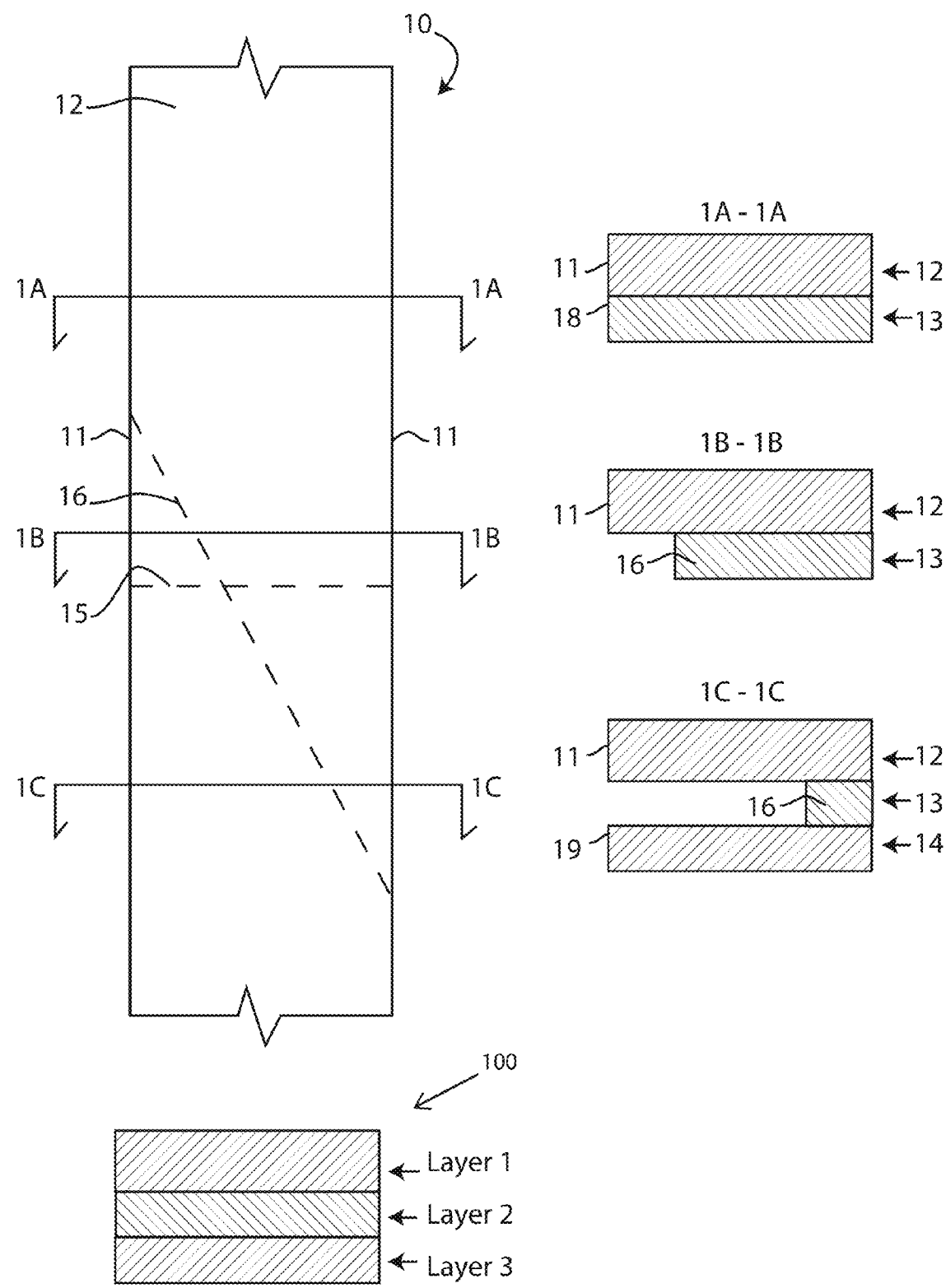
FIG. 1 shows a portion of a layered component of an orthosis and its applicable cross-sections before the orthosis is put under pressure, in accord with embodiments.

As noted above, fiber-reinforced laminate orthoses may be provided in embodiments. The shape, relative orientation, and positioning of layers comprising the orthoses may be configured and assembled in embodiments to manage the distribution of external static and dynamic loads through and within the orthosis. The shape, including their geometrical outline, thickness, and other external dimensions; relative orientation; and positioning of the layers or lamina may also be configured and assembled to manage the amount of loading stresses and loading strains developed in various areas of the orthosis. Likewise, fiber orientation in both unidirectional composite layers and bidirectional composite layers may also be considered in embodiments and may play a role in orthosis performance in embodiments.

Embodiments may include AFOs, which should be understood to include KAFOs, dynamic AFOs, dynamic KAFOs, etc., made of fiber-reinforced composites. These fiber-reinforced composite AFOs can be manufactured through a number of methods. For example, dry fiber layup techniques, as well as prepreg layup, can be used. Fibers suitable for reinforcement of AFOs may include carbon, glass, and aramid fibers, among others. Regardless of whether dry fiber techniques or prepreg layup or other manufacturing techniques are used, different types of fiber orientation can be used. Layers may also be classified by identifying them as Unidirectional (UD) and Bidirectional (BD) layers. BD layers can also be referred to as weaves. The matrix and additives used to construct the orthosis in embodiments may also vary, for instance both thermo-set resins, such as epoxy, as well as thermo-plastic resins, such as polyamide, may be used. Additives can come in numerous forms, an example being colorant.

In embodiments having fiber-reinforced composites, the load may be carried in the direction of the fiber. Creating a functional and durable AFO may combine brace design and fiber orientation. Brace design of AFO embodiments may be considered in three-dimensions in order to adapt to the organic shape of the lower leg and foot. The fiber orientation may also preferably align with the load applied to the lower leg and foot. In the case of an AFO, the brace may be designed in embodiments to mimic or trace the ankle joint as well as hind-foot, mid-foot, and fore-foot joints.

In embodiments, an AFO may extend both above and below the ankle. In the lower leg, below the knee, most motion takes place at the ankle joint itself or below the ankle.

As the upper part of an AFO can guide the Tibia and Fibula, whereas the lower part of an AFO is regularly more dynamic to meet the movements normally taking place within the ankle and foot, embodiments may promote support to the lower leg and the ankle. In calculating load and its ratio to maximum composite laminate strength when damage initiation occurs ("load to maximum strength ratio" as used throughout), the complex load case of an AFO may be considered as movements in three different planes: sagittal, frontal (coronal), and transverse. In the sagittal plane, movements such as flexion and extension take place, for example, plantar flexion and dorsiflexion of the ankle joint. In the frontal plane, movements such as lateral or medial tilting take place, for example eversion and inversion. In the transverse plane, rotational movements take place. Also, the three planes of movements could be transferred into a coordinate system. For example, the sagittal plane could be the X-axis, the frontal plane could be the Y-axis and the transverse plane the Z-axis. Each of these movements may be considered in orientation of layers and other adjustments provided in embodiments herein.

In embodiments, one or more composite layers used in constructing an orthosis may share similar or identical aspects to some or all other layers. These aspects may include being partially or fully symmetrical to some or all layers in certain aspects and being unique to some or all layers in certain aspects. The layers may be formed and assembled such that the ratio of the maximum composite laminate strength for an area of the orthosis and loads expected for the coinciding area being evaluated is larger than one. Through controlling maximum composite laminate strength (up or down) for various areas of an orthosis, especially when compared to the same ratio for other areas of the orthosis, safety zones or loading zones, may be created in the orthosis. Furthermore, the orthosis may function in embodiments such that it is better adapted for the relative movement above the ankle of a wearer and is better adapted for the relative movement at or below the ankle of a wearer.

Safety zones in the orthosis may be created in embodiments through layer configuration, composition, orientation, and placement, as well as through fiber orientation. In embodiments, a ratio between expected loads to maximum composite laminate strength (as used herein "load to maximum strength ratio") may be considered for various areas of an orthosis. This ratio is preferably lower than one for a particular area because a value of one or more signifies composite damage initiation. Areas with lower load to maximum strength ratios may be considered safety zones while areas with load to maximum strength ratios closer to one may be considered loading zones. The ratio between safety zones and loading zones, or other areas, may also be considered to evaluate expected orthosis performance. In addition, selective placement of safety zones, loading zones, and their combination, may be used to manage orthosis performance.

In embodiments, safety zones, for example, may be located at upper portions of an Ankle Foot Orthotic (AFO), where the strut is connected to a lower leg connector as well as in areas shared by the strut and the lower leg connector. Likewise, loading zones, may themselves be located in embodiments, at lower portions of an AFO strut close to where the strut connects to a footplate. The position and difference in the magnitude between the load to maximum strength ratio of the safety zone and the load to maximum strength ratio of the loading zone can serve to both predict and tailor the performance of the orthosis, as well as the ability to manage composite damage initiation.

In embodiments, layers may be configured such that load to maximum strength ratios are managed to be lower in safety zones and higher in loading zones. Still further, in embodiments, comparative ratios between load to maximum strength ratios in loading zones located in the lower end of the strut when compared with safety zones located at the upper end of a strut in the same orthosis may preferably above 1.0 in embodiments. This loading zone to safety zone ratio can serve to reflect expected orthosis performance.

Layers of the composite comprising an orthosis in embodiments can include reinforcing fiber and may comprise geometrical shapes having modified or nonorthogonal proximal and/or distal ends or both. The reinforcing fiber employed in layers of embodiments may be UD or BD, and the reinforcing fibers employed may be carbon, glass, or aramid, among other fibers. The composite layers may also be stacked in embodiments, such that the layers do not fully traverse components comprising an orthosis and may have unique proximal and/or distal ends that serve to improve load to maximum strength ratio in the area where the end is positioned. This revised load to maximum strength ratio may have a corresponding effect whereby other areas of the orthosis are subject to more stresses during expected loading. This combination of the revised load to maximum strength ratio and the transfer of stresses to elsewhere in the orthosis can serve to promote safety zones, loading zones, and to effect orthotic performance.

In embodiments, composite fiber reinforced layers may be shaped or modified to include discernible internal cutouts, open areas, or spaces, such as ovals, circles, rectangles, and hourglasses, as well as to include other symmetrical and nonsymmetrical cutouts, open areas, or spaces. The layers may also include proximal and/or distal ends shaped into points, proximal and/or distal ends with nonlinear edges, and/or proximal and/or distal ends being curved or notched or otherwise not being purely orthogonal to a side edge of the layer. These various layer modifications, and combinations of them, when introduced into one or more composite fiber reinforced layers and when oriented with layers having similar or differing modifications may serve to effect load to maximum strength ratio in and around the area of the modifications.

In embodiments described herein and others not described, supporting struts, strut footplate interfaces, opposing thirds of a strut or footplate, and other areas of an orthosis, can each have the modified layers discussed herein and may each employ modifications affecting the load to maximum strength ratio in various areas.

In embodiments, the modifications of one or a stack of reinforced layers may solely be present in proximal and/or distal portions of the layers. In other words, and for example, in one or more layers of a reinforced composite layer used when manufacturing a composite ankle foot orthosis, the upper two-thirds of the layer may be symmetrical and rectangular but the lower third of one or several layers may have an arrow shaped end. Likewise, the reverse may also be employed in embodiments. Still further, an arrow shaped distal end may not reach the footplate or another component of the orthosis such that a floating joint is created. This arrow configuration and a related floating joint may serve to manage loading in the orthosis by managing load to maximum strength ratio of various areas of the orthosis.

As noted, additional similar or identical layers may also be used in the same orientation, with the same fiber orientation, and in other orientations to further manage load to maximum strength ratio of areas in the AFO or other orthosis embodiment. For example, additional layers with modified proximal and/or distal ends may be employed for controlling the magnitude and location of tolerable material stresses expected to be developed in the orthosis. Likewise, multiple floating joints or butt joints may also be used to further manage the magnitude and loading of tolerable material stresses expected to be developed in the orthosis and the relationship between these expected stress areas and maximum composite laminate strength of the same area. Maximum composite laminate strength design loads may be predicted using various prediction tools employing finite element analysis including Tsai-Hill and Tsai-Wu or other failure analysis criteria suitable for composite laminates.

Thus, in embodiments, an orthosis may be designed such that the ratio of expected stresses from loads, as related to the maximum composite tolerable laminate strength of target areas, may be decreased in certain areas of the orthosis where lower stresses are preferred and may be increased in other areas of the orthosis where higher material stresses are acceptable. Moreover, in embodiments, by changing or expanding the length and surface areas of the proximal ends and/or distal ends of one or more layers, developed stresses may be reduced in that area or modified in other areas, and improved ratios between expected external loads and maximum composite laminate strength to damage initiation may be provided in this area or other areas of an orthosis.

FIG. 1 shows a section 10 of a layered composite orthotic in accord with embodiments. The section 10 of the composite orthosis is shown with three layers, a top layer 12, a middle layer 13, and a bottom layer 14. As can be seen in end view 100, all three layers are shown having the same width and side edges that are parallel and spaced the same distance apart as well. The top layer 12 is shown with parallel sides 11 and is shown to span the entire length of the orthosis section 10 shown in FIG. 1. The middle layer 13 is also shown with parallel sides 18 that have the same width as the top layer 12 and has a distal end with a straight angled edge 16. Bottom layer 14 is also shown as having parallel sides 19 for its entire length where these sides are the same width as top layer 12 and the middle layer 13. The top end of bottom layer 14 is shown to have an edge 15 that is orthogonal to both of its side edges and is shown to extend over and overlap the top layer 12 and the middle layer 13. In embodiments, one or more of these layers may be made of a fiber reinforced composite including unitary fiber reinforced composites and BD fiber reinforced composites, where the fibers are BD, having two orientations.

Three section lines and the applicable cross-sections are also shown in FIG. 1. The section line $1_A$-$1_A$ of FIG. 1 and the corresponding sectional view $1_A$-$1_A$ in FIG. 1 shows that layers 12 and 13 have the same width but a different thickness at that section line, while section lines $1_B$-$1_B$ shows that layers 12 and 13 have different width and a different thickness at section line $1_B$-$1_B$. Also evident in FIG. 1, as shown with section line $1_C$-$1_C$, is that the edge 16 at the distal end of layer 13 is not orthogonal to the sides of layer 13 and, in this instance, is angled in relation to its side edges. This angled edge 16, which is positioned consistent with the layer above it and below it, serves to affect the maximum composite laminate strength and normalized design loads in and around the edge 16 and its adjoining layers. In other words, the configuration and orientation of the edge 16 may serve to lower the amount of stress developed above the edge 16 relative to the maximum composite laminate strength. The edge 16 may also serve to provide for relative increased or decreased rigidity that can affect strain development in other areas of the orthotic. This development of strain in other areas may serve to develop magnitudes of stress away from the angled edge and, moreover, to develop magnitudes of stress that are closer to the peak acceptable stresses in a different area of the orthosis, an area targeted to be closer to its peak stress capabilities under loading than the area adjacent and above the angled edge.

Figure 2:
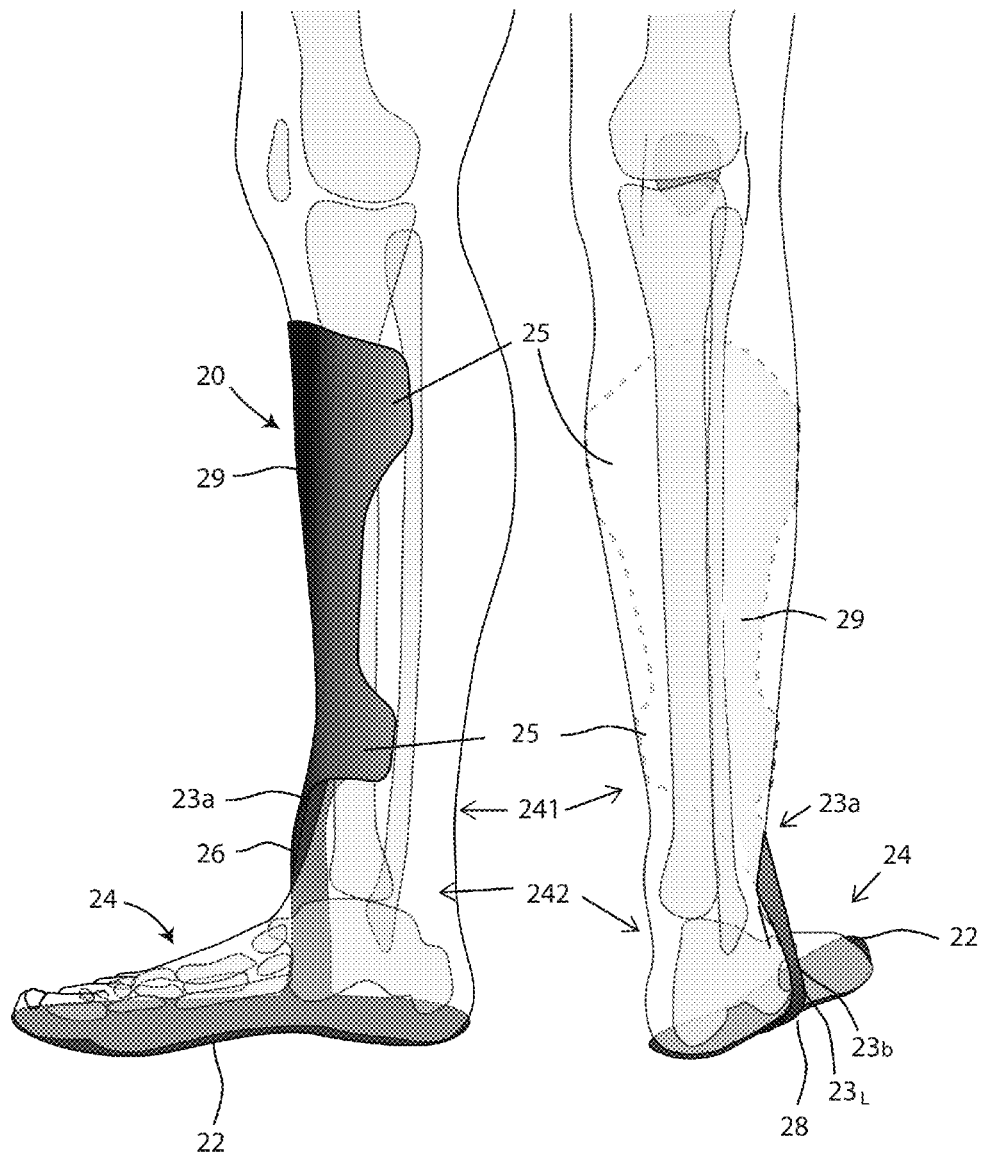
FIG. 2 shows a medial side and posterior perspective view of an ankle foot orthosis mounted on a lower leg of a user in accord with embodiments.

FIG. 2 shows perspective views of a composite laminate AFO 20 mounted on the lower leg of a user from the medial side of the lower leg of the user and from the posterior side of the lower leg of the user as may be employed in embodiments. The composite laminate AFO 20 includes a lower leg support 29, a strut 26, a footplate 22, and four alignment ears 25. While only a single strut is shown in FIG.

2, AFO embodiments may also employ two struts, either on the same side of the ankle of a user or on opposite sides of the ankle of the user or behind the lower leg of a user.

FIG. 2 also shows how the lower leg 241, ankle 242, and foot 24 of a user may be oriented in the orthotic and supported by the orthotic. As can also be seen, the ankle 242 of the user is positioned below the lower leg support 29 and adjacent the strut 26 of the AFO 20 and above the footplate 22. The footplate 22 of the AFO may be somewhat flat and may reside under most or all of the sole of the foot of a user. In KAFO embodiments, the lower leg support including some of the strut may extend further up the lower leg of the user and may be secured around portions of the knee joint of a wearer. The lower end 28 of the strut 26 may extend into or otherwise connect with the footplate 22 of the AFO 20.

As related to loading that may occur and for accommodations of designs and teachings in embodiments, during normal gait the ankle motion during a stride may involve a range of plantar flexion up to 20° or so and dorsiflexion up to 10° or so. In the subtalar joint, normal gait may involve a range of inversion (medial tilt) up to 10° or so and eversion (lateral tilt) up to 10° or so. These degrees may change substantially if the activity "normal gait" is changed to another activity, such as "descending stairs." As such, loading and accommodations of design may be further accommodated. As to range of motion, in the latter activity, the movement dorsiflexion may reach a value of 35° or so. Comparatively, if the activity performed is "ascend stair" the plantar flexion may reach 40° or so. Range of motion along different planes or axis may also be affected by deficiencies such as neuromuscular weaknesses or diseases, neurological disorders, or birth defects among others. Depending on how the deficiencies present, the impaired gait may involve limitation to the range of motion as well as extended range of motion. Both normal and impaired gait are also affected by movements from the complexity of joints above the ankle, knees and hip belonging to the lower extremities, as well as pelvis and trunk. As a step progresses, the whole body propels forwards and movements take place in all three planes. A composite AFO in accord with embodiments can serve to address these and other movements in all three planes and for these various use and loading scenarios whereby the fiber layup should preferably meet with load situations as well as with anatomical shapes.

Figure 3:
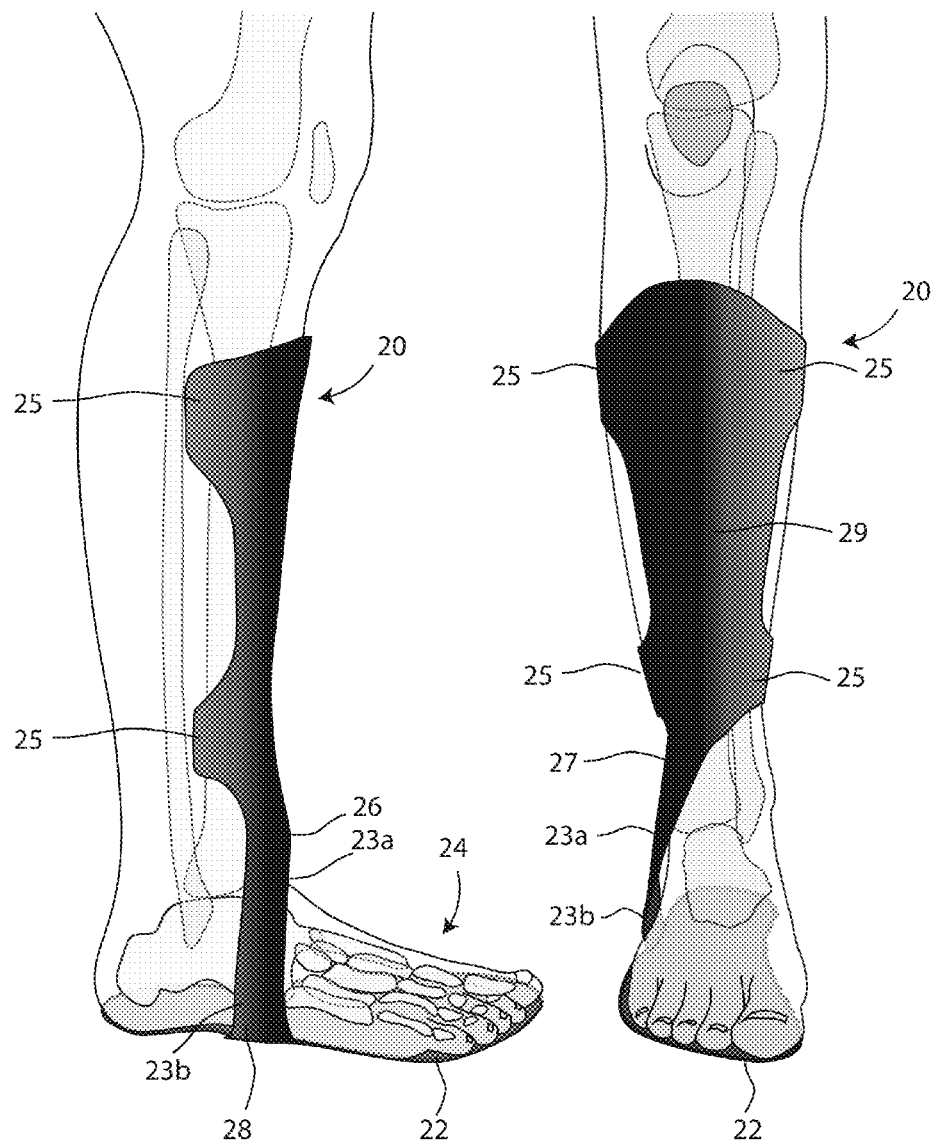
FIG. 3 shows a lateral side and anterior perspective view of an ankle foot orthosis mounted on a lower leg of a user in accord with embodiments.

FIG. 3 also shows perspective views of the same composite laminate AFO 20 mounted on the lower leg of a user as in FIG. 2. In FIG. 3, however, lateral and anterior views are shown and the upper third of the strut 26 is labeled 27. The views of FIG. 3 show how a lower leg support 29, strut 26, footplate 22, and four alignment ears 25 may conform with the medial and lateral side of the lower leg and foot of a wearer. Safety zone 23a and loading zone 23b are shown to be located on various areas of the strut 26 in FIGS. 2 and 3. However, these zones may be in different locations, as well as in other embodiments, for example, the zones may be closer together, both in the middle third of the strut 26, further apart but still closer to footplate 22, in the footplate 22, and well into the area also occupied by the lower leg support 29.

FIGS. 2 and 3 show safety zones and loading zones as may be created or included in accordance with embodiments. These safety zones are shown at 23a in FIGS. 2-3 while the loading zones are shown at 23b of these same Figures as well as $23_L$ of FIG. 3. The safety and loading zones may be located elsewhere in embodiments as well.

Figure 4A:
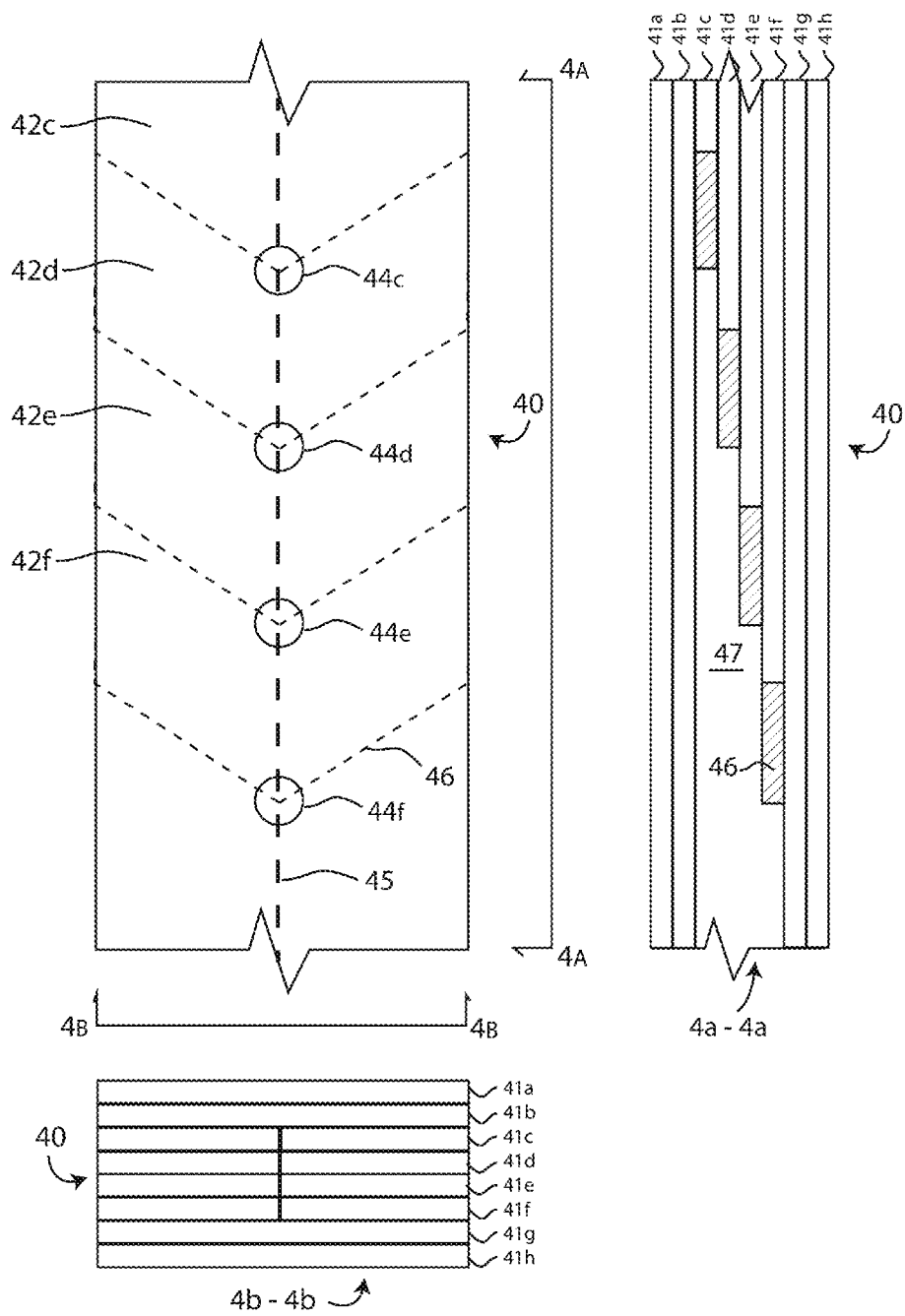
FIG. 4A shows a portion of a layered component of an orthosis and its applicable cross-sections before the orthosis is put under pressure, in accord with embodiments.

FIG. 4A shows a section of a lower leg support and multi-layer strut 40 viewable looking straight down at it, which is often referred to as a plan view, and before the strut 40 has been placed under pressure, as may be employed in an AFO or other orthosis embodiment. Also shown are cross-sectional perspective view lines $4_A$-$4_A$ and $4_B$-$4_B$ of the lower leg support and multi-layer strut 40, which coincide with the perspective views shown in side view $4_a$-$4_a$ and end view $4_b$-$4_b$. Section 40 may be a portion of the strut 26 and lower leg support 29 shown in FIGS. 2-3 and may be extended to end in the top, middle, or bottom third of the strut. Shown in views 4a-4a and 4b-4b are eight layers of fiber reinforced composite materials. The top two layers 41a, 41b and the bottom two layers 41g, 41h span the entire portion of the strut section 40 shown in FIG. 4A.

Comparatively, fiber reinforced composite layers 41c, 41d, 41e, and 41f do not span the entire length of the section shown. As can be seen each of layers 41c-41f extend from the top of the strut 40 and have distal ends 42c, 42d, 42e, and 42f that do not reach the bottom of the portion of the strut 40 shown in FIGS. 2-3. Thus, in embodiments, layers of the strut of an orthosis embodiment extending from a lower leg support may not reach the footplate 22 of an orthosis and may end partway through a strut or other connecting member. The apex of distal ends 42c to 42f are indicated at 44c-44e, edge of distal end 42f is identified at 46 and center line 45 is also shown.

The multi-layer strut 40 is shown to include eight composite layers 41a-41h. In FIG. 4A layers 41a, 41b, 41g and 41h are layers comprising BD fibers. Likewise, inner layers 41c, 41d, 41e, and 41f, which each have distal ends terminating in the section, are layers also comprising BD fibers. In embodiments, however, outer layers, layers closer to the outside or on the outside and inner layers, layers closer to the center or core and not on the outside, may also comprise UD fiber layers.

The distal ends 42c, 42d, 42e, and 42f are shown to have different ending points along the length of the strut section 40. Thus, the layers 42c, 42d, 42e, and 42f each extend a different amount down into the strut support 40. Also evident in FIG. 4A is that each distal end has an apex point 44 that lies along the center line 45 of the strut 40 and is formed by the intersection of the two edges of the distal end of the layer. As can also be seen, the distal end of layers 41c, 41d, 41e, and 41f are uniformly spaced apart from the distal end of the layer immediately above and immediately below. These four layers, with the triangular shaped distal ends 42c, 42d, 42e, and 42f, may be considered to form the shape of a chevron. In still further embodiments some or all distal ends may terminate in other configurations as well. For example, the chevrons may be pointing upward rather than downward as shown in FIG. 4A. Thus, some ends may be pointing upwards while others may be pointing downward or all are pointing one in one or the other direction in embodiments.

Cross-sectional view $4_a$-$4_a$ shows layers in strut 40 before pressure has been applied to force the layers closer together. Once pressure is applied, the space 47 will be substantially removed. The edges 46 of the distal ends 42c, 42d, 42e, and 42f, of layers 41c, 41d, 41e, and 41f are evident in cross-section $4_a$-$4_a$.

Cross-section view 4b-4b shows a view from perspective line $4_B$-$4_B$. As can be seen in this sectional view, the apexes 44 are located in the center of the distal edges 46 for each of the layers 41c, 41d, 41e, and 41f.

Figure 4B:
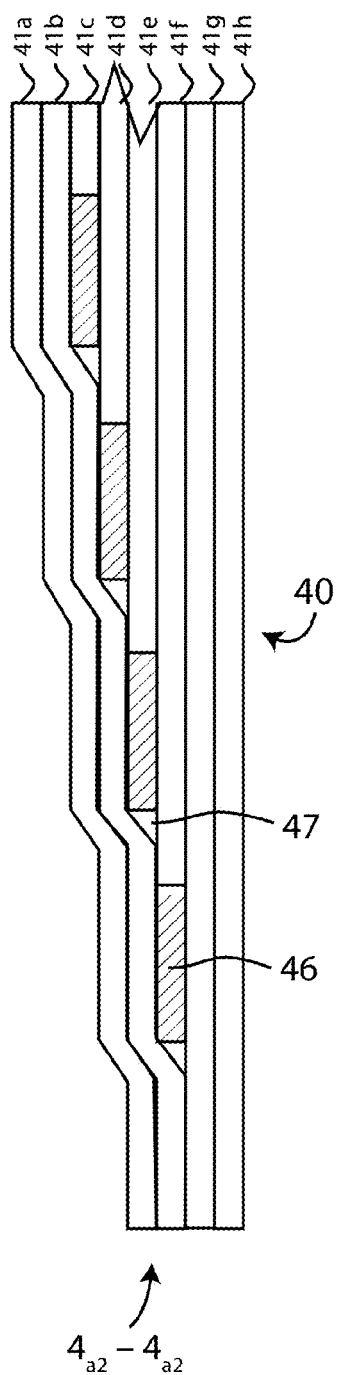
FIG. 4B shows the layered component of FIG. 4A after the orthosis is put under pressure, in accord with embodiments.

In FIG. 4B, cross-section view $4_{a2}$-$4_{a2}$ shows layers in strut 40 after pressure has been applied to force the layers closer together. Areas 47 of matrix with little if any reinforcing fibers may remain after pressure is applied. Like in FIG. 3, in embodiments, the strut 40 of FIGS. 4A and 4B may also include some or all of a lower leg support.

Figure 5:
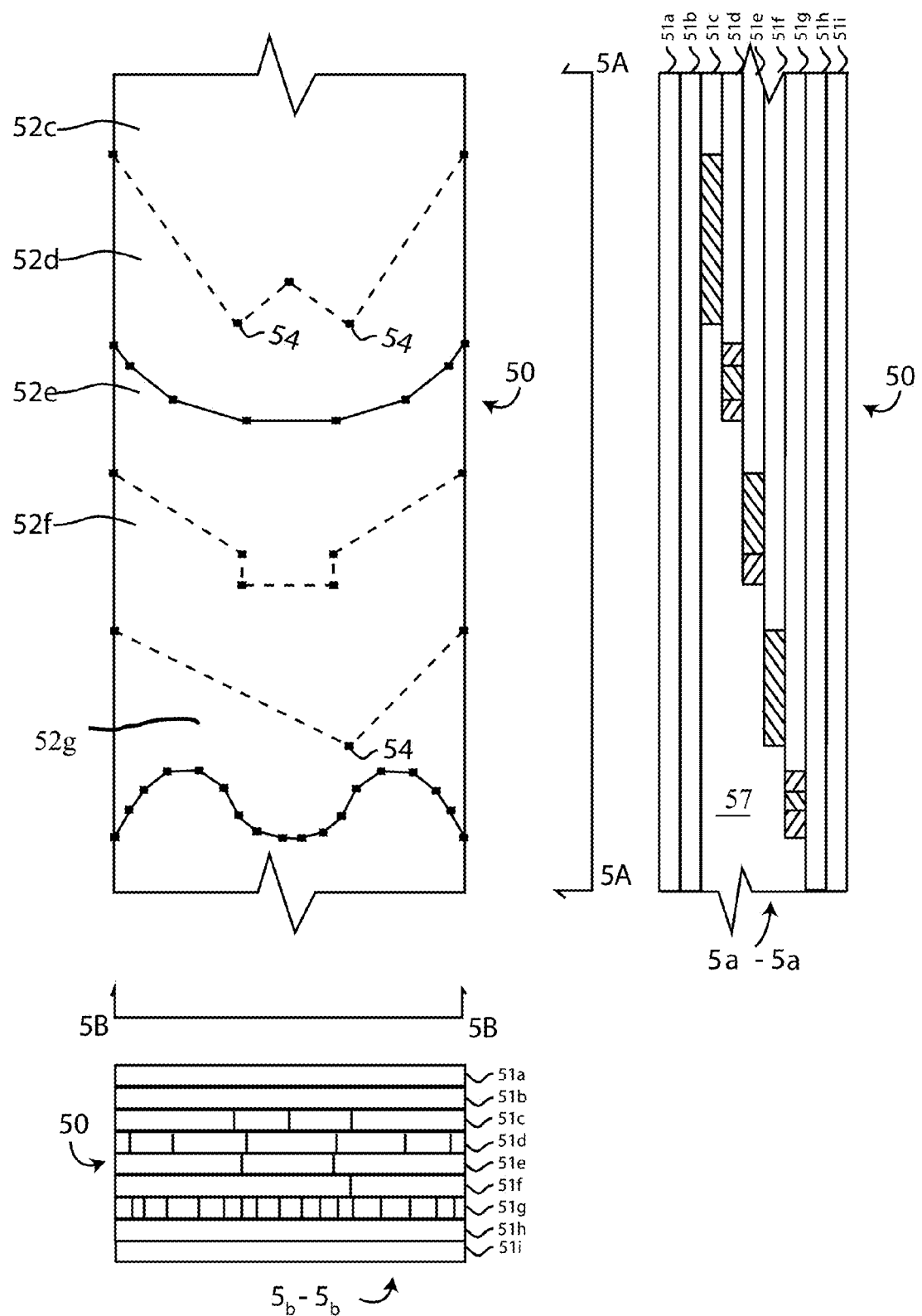
FIG. 5 shows a portion of a layered component of an orthosis and its applicable cross-sections before the orthosis is put under pressure, in accord with embodiments.

FIG. 5 is similar to FIG. 4 in that FIG. 5 shows a section of a strut 50 with multiple layers 51a-51i, where internal layers of these multiple layers have distal ends 52c-52g that do not extend fully throughout the length of the strut 50. Also like FIG. 4, the layers are shown in cross-section 5a-5a before pressure has been applied to them to urge them closer together. Also like FIG. 4, fiber reinforcing may be present in each of the layers and fiber may be UD or BD or oriented randomly. A distinguishing feature in FIG. 5 versus FIG. 4 is that the distal ends of the layers 51c-51g do not have triangular ends with their points laying along a central axis of the strut as in FIG. 4. Rather, the distal ends of layers 51c-51g have various configurations, some of which are centered on the geometrical center line of the strut and some of which are not. As can be seen, these various configurations may be w-shaped as in distal end 52c, may be multiple line segments as in distal end 52d, may be triangular as in distal end 52f, may be rectangular as in distal 52e, and may be curved as in distal end 52g. Apexs 54 are also shown in FIG. 5. The ends may also be configured to be the inverse of those shown and other configurations as well in embodiments. Still further, embodiments may also include proximal ends configured with various shapes and truncations as show in FIGS. 4A-4B, FIG. 5, and FIG. 7 and consistent with the teachings herein.

The edges of the various distal ends are shown in cross-sectional view 5a-5a and 5b-5b. The side cross-sectional view 5a-5a shows how a gap 57 may exist before pressure is applied to urge the layers together. End cross-sectional view 5b-5b also shows how layers 51a and 51b may not be folded down or towards layers 51c-51i until pressure is applied to bring the layers together. Like in FIG. 3, in embodiments, the strut 50 of FIG. 5 may also include some or all of a lower leg support. Also, the struts of each embodiment described, as well as others, should be considered to be able to be in front of, to the side of and/or behind the ankle of a wearer.

Figure 6:
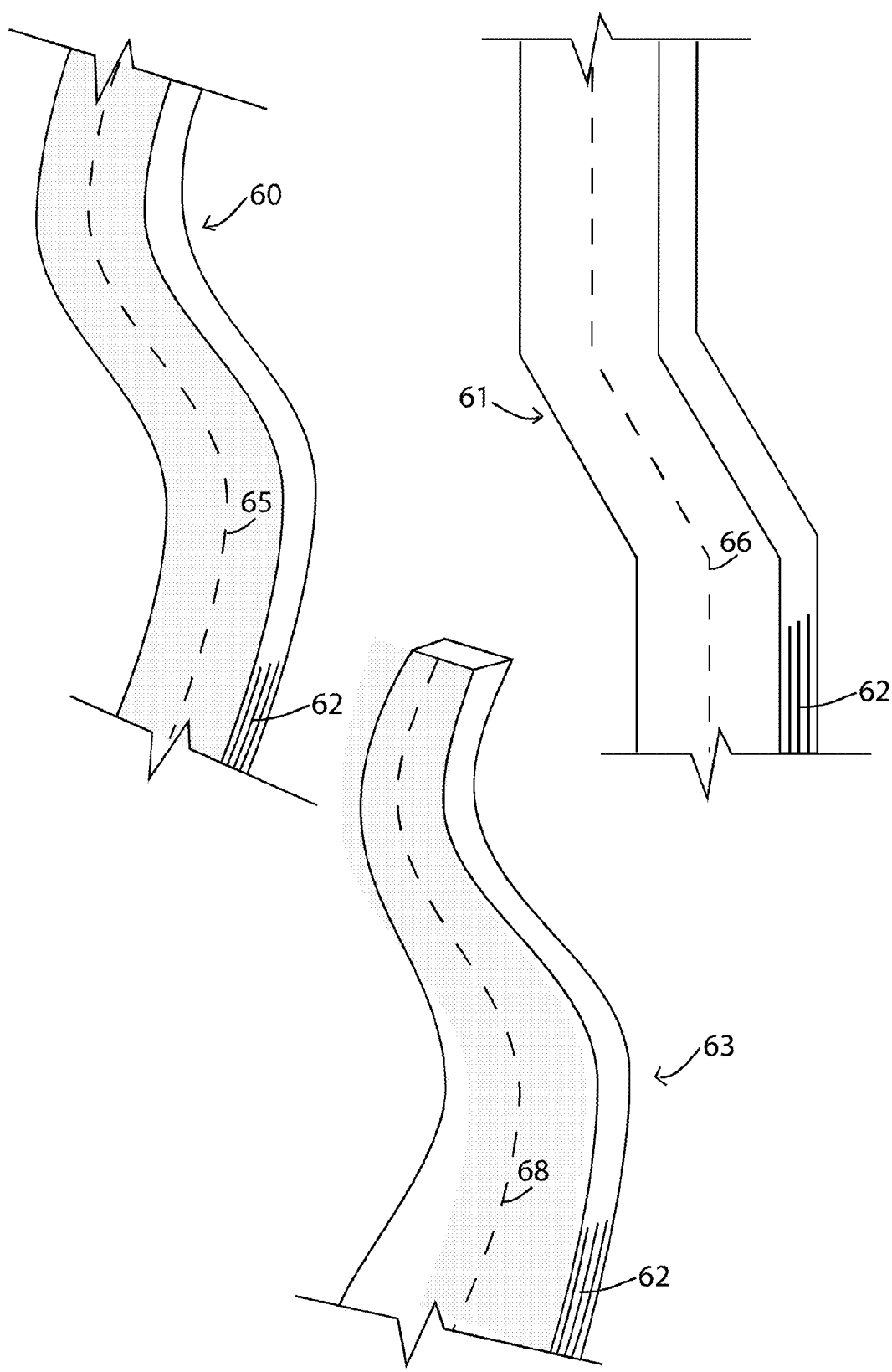
FIG. 6 shows perspective views of laminate components with delineated geometric center lines as may be employed in embodiments.

FIG. 6 shows exemplary struts 60, 61, and 63 as may be assembled in accord with embodiments. These struts may be employed in an orthosis and may comprise multiple layers 62 of fiber reinforced composites. Evident in FIG. 6 are the center lines 65, 66, and 68 of the struts shown in the figure. As can be seen, these center lines 65, 66, and 68 are centered geometrically along the length of the struts and coincide with the turns and bends of the struts. In embodiments, one or more layers may have proximal and/or distal ends that terminate along the length of a strut and have their distal end apex or center v-groove or other center geometry centered over the center line of a strut. In embodiments, some layer proximal and/or distal ends may be centered over the geometrical center while other layers may not. FIG. 5 shows this as distal end 52d and 52e, which are centered over the geometrical center 55 of strut 50, while distal end 52f is not.

Figure 7:
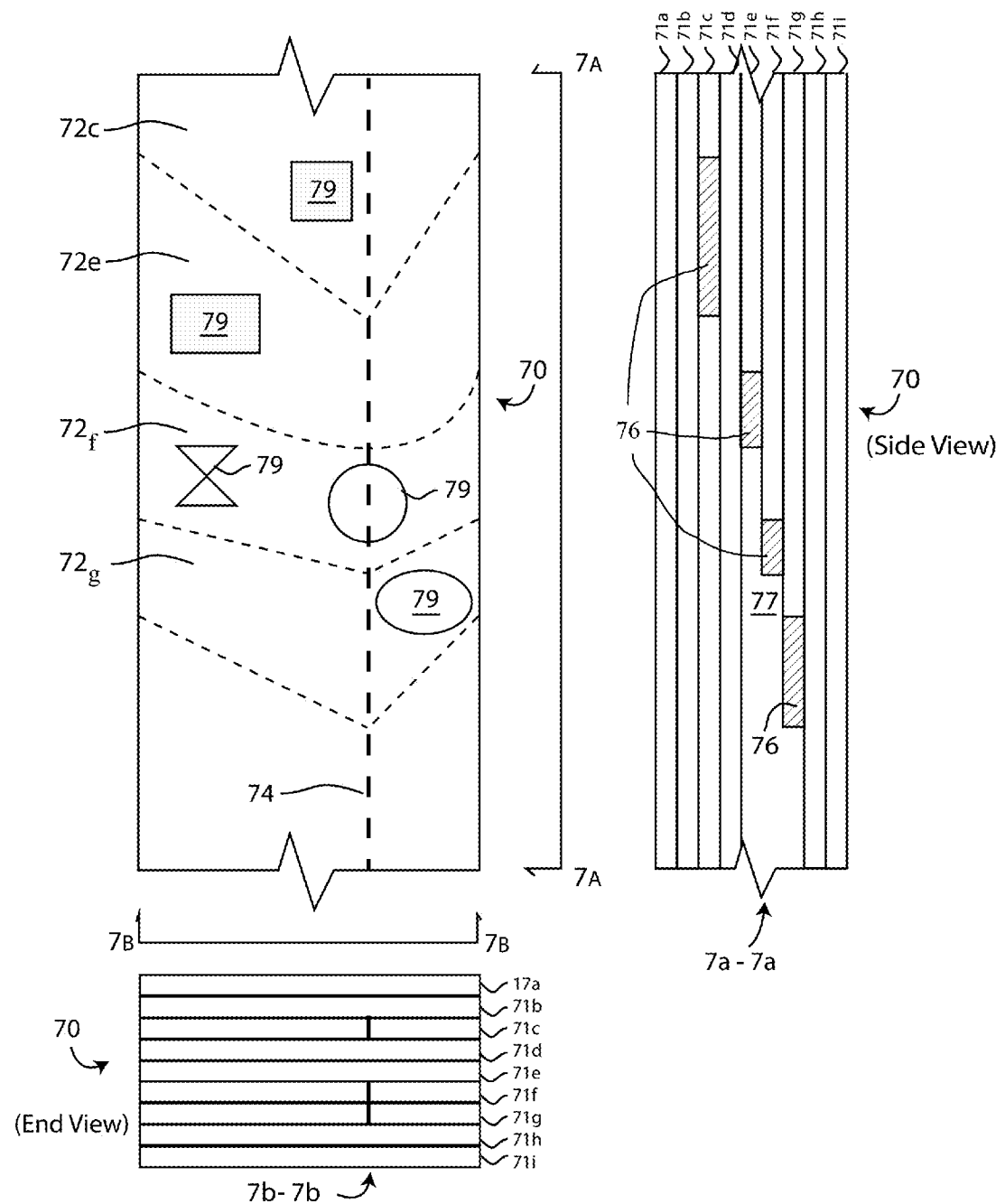
FIG. 7 shows a portion of a layered component of an orthosis and its applicable cross-sections before the orthosis is put under pressure, in accord with embodiments.

FIG. 7 shows that the edges 76 of the various ends of layers comprising a strut may have still further configurations and may be centered on the strut along a line that does not lay in the geometrical center of the strut 70. Visible in FIG. 7 is the strut 70 in top view, side view, and end view, as well as perspective reference lines 7A-7A and 7B-7B and their associated perspective views $7_a$-$7_a$ and $7_b$-$7_b$, as well as distal ends 72c, 72e, 72f, and 72g, and stacked layers 71a, 71b, 71c, 71d, 71e, 71f, 71g, 71h, and 71i.

Figure 8:
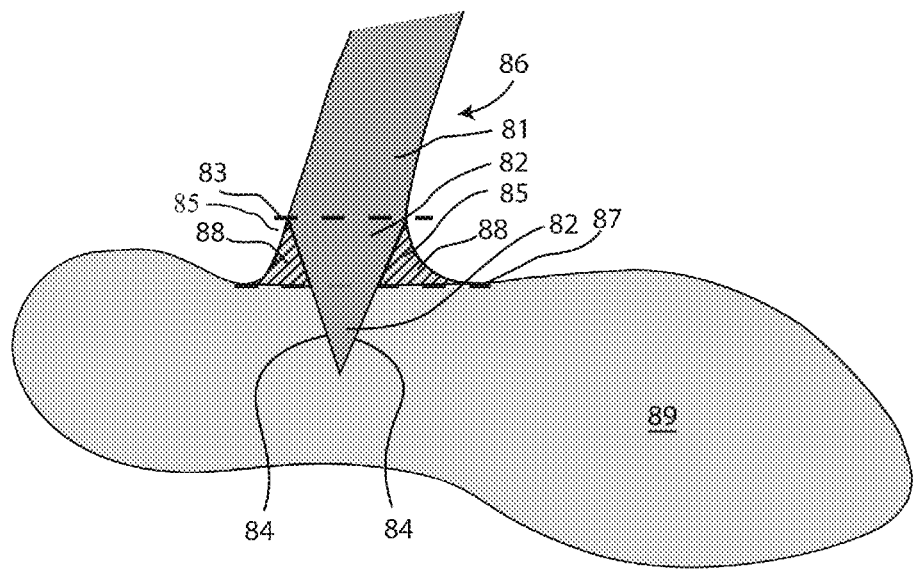
FIG. 8 shows a perspective bottom view of layers of a laminate orthosis as may be employed in embodiments.

In FIG. 7, as well as in FIGS. 4 and 5, it should be understood that distal ends of certain layers may extend or may not extend in any way into the foot plate of an AFO or KAFO. In some embodiments, the distal end of a layer may extend partially into the footplate, as shown in FIG. 8. Likewise, if proximal ends are configured with apexes, points, or other geometry as taught herein, these ends may or may not extend up through the most proximal portions of the orthosis or other layered composite employing embodiments described or taught herein.

As can be seen in FIGS. 4-5 and 7, in embodiments as the layers are stacked and before pressure is applied an open area 47, 57, and 77, without material including fiber reinforcement, may be created because all the layers do not extend over exactly the same area. This absence of uniform reinforcement and material can work in conjunction with the apex or other design shape at the distal end of one or more layers to manage and control the distribution of loading and its application in relation to the composite laminate strength of various areas of an orthosis. By organizing and configuring composite materials in this fashion embodiments may provide for the ratio of loading when compared to the maximum composite laminate strength to be higher in some areas of the orthotic and lower in other areas of the orthotic. In certain embodiments this load to maximum strength ratio may be larger in lower areas of the strut and may be smaller in higher areas of the strut.

In embodiments, the nonorthogonal shape, staggered placement, and uniform or nonuniform placement of fiber reinforced composite material may serve to place larger relative loading on other areas of an orthotic rather than directly around the modified edge of the proximal or distal end of a layer. Also, the apex configuration itself can serve to focus loading and resulting stresses and strains.

Still further, as is evident in FIGS. 4A, 4B, 5, and 7, embodiments may contain many load management layers, such as 41c-41f, 51c-51g, and 71c-71g. As can be seen in FIGS. 4A, 4B, 5, and 7, in embodiments, the load management layers may share the same overall dimensions but extend further and further down the strut of the AFO. Also, the load management layers may not reach all the way to a foot plate of an AFO in embodiments, but may, instead, create a floating joint with their proximal or distal end. Also noticeable is that the layers may be staggered with outer layers extending the shortest distance down a component, such as a strut, and lower layers extending a further distance down a strut or other component. For those distal ends with points or an apex, or an inverted geometrical end such as a v-grove, they may lay along a geometrical center line or a shared line not on the geometric center. It should also be realized that other layers may be present in embodiments and that layers may be removed and differ from those shown wherein. For example, additional layers may be placed atop those shown in FIG. 4 and may extend continuously from the lower leg support to the footplate of an AFO. Still further it should be understood that the distal ends of embodiments shown in FIGS. 4A, 4B, 5, and 7 show edges having a length greater than the width of their own layer. Also, some or all of the management layers may also be positioned in reverse to those shown in FIGS. 4A, 4B, 5, and 7. For instance, in this reverse example, the proximal ends of one or more layers may not reach up or through the entirety of a layered component.

Cutouts 79 are also evident in FIG. 7. As can be seen, the cutouts may have various shapes and may be positioned in various ways. This positioning may include being on one side of a center line, being on a center line, and having more than one cutout at a distal end a proximal end or both.

FIG. 8 shows a portion of an orthosis as may be employed in embodiments. The footplate 89 and strut 86 intersection is shown in FIG. 8. Also visible in FIG. 8 is a load management layer 81 having a tapered end 82 that begins after line 83 and extends from the strut 86 through a crease or transition 87, and to the footplate 89. Other layer material 88 is also shown in FIG. 8 where this other material 88 also forms portions of the footplate 89 strut 86 interface and may be for structural and/or aesthetic reasons.

In embodiments the layer 81 may extend downwardly into the footplate about 22 mm past line 83 and to the apex and have tapered edges 84 that are each about 24 mm or so. The distance between the sides of the strut is shown to be smaller than 22 mm so that the length of the edges 84 is greater than the distance between the sides. As can be seen in FIG. 8, the illustrated portion of the management layer shares the same width as the strut 86 then becomes narrower than the strut, not covering areas 85 and extending into footplate 89. The combined absence of layer 81 from the triangular areas 85 and layer 81's tapered end may be considered to contribute to load management in the orthosis as would be the other layer end configurations and placement as discussed herein. In embodiments, as a strut of an AFO deflects during use the absence of a layer over the triangular area 85 or the presence of composite material at some locations and not others may serve to provide some flexibility as well as to manage loads such that experienced loads or expected loads near maximum composite laminate strength to varying degrees in different areas of the orthosis.

As discussed herein, in embodiments, the management of expected design loads relative to maximum composite laminate strengths may result in safety zones being created where orthosis failure or other damage is less likely to occur in that area than in another area. For example, failure or other damage may be less prone to occur when the load to maximum strength ratio in one zone is less than load to maximum strength ratio in another zone during expected loading. Likewise, in embodiments, relative safety ratios may also be identified and maintained in other areas of an orthosis, such that several specific areas may be more or less prone to deformation or failure when compared to other areas of the strut or the orthosis. In embodiments these zones may be adjacent to each other and in embodiments they may be spaced apart from one another.

With respect to serving as a pseudo-joint, i.e., supporting the ankle or other joint, targeted flexibility, localized below or around the ankle, may also be provided by embodiments. For example, decreased flexibility of the orthosis above the ankle and increased flexibility above and around the ankle, using principles and teachings provided herein, may provide benefits to a wearer.

Certain AFO mounting principles when considering loads may be employed in embodiments. For example, a footplate in an AFO may be mounted during testing in such a way for uniform simulated testing. As an example, applying a displacement of the lower leg support forward relative the footplate and also displace the lower leg support backwards relative the footplate the displacement may be considered to be rotating around a point where the human ankle joint is positioned. Under these loading securements and conditions the location of safety zones and loading zones may be evaluated where damage initiation testing is employed to indicate maximum composite laminate strength.

For example, employing damage initiation failure criteria such as Tsai-Hill, Tsai-Wu or other failure analysis criteria suitable for composite laminates, when bending an AFO 7 degrees forward a load to maximum strength ratio may be created in the range of 0.29 or so. Likewise, when bending the AFO in the opposite direction a load to maximum strength ratio may be created in a range around 0.40. These ratios may then be compared to create a comparison ratio, which in this instance is 1.379. In a similar way bending the AFO backwards with 9 degrees employing the same load to maximum strength ratio may give a range that includes 0.54 or so and bending in the opposite direction may provide a load to maximum strength ratio including 0.62 or so. The comparison of these ratios is shown to be about 1.15 and may be this or other ratios in embodiments.

As explained and applied throughout, fiber reinforcement may be present in none, some, or all of the layers. This reinforcement may have fibers running in a single direction, i.e., UD and may have fibers running in two directions, i.e., BD such as in a two-dimensional weave. The matrixes interfacing with the support fiber may vary and may include thermo-set or thermo-plastic such as epoxy and polyamide, as well as other suitable matrixes.

Although the foregoing description is directed to certain embodiments of the invention, it is noted that other variations and modifications will be apparent to those skilled in the art provided with the disclosure herein, and may be made without departing from the spirit or scope of the invention. Moreover, features described in connection with one embodiment of the invention may be used in conjunction with other embodiments, even if not explicitly stated in the foregoing. The described embodiments are to be considered in all respects only as illustrative and not restrictive.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" and/or "comprising," when used in this specification, specific the presence of stated features, integers, steps, operations, elements, and/or components, but do not preclude the presence or addition of one or more other features, integers, steps, operation, elements, components, and/or groups thereof.

The corresponding structures, material, acts, and equivalents of any means or steps plus function elements in the claims below are intended to include any structure, material or act for performing the function in combination with other claimed elements are specifically claimed. The description of the present invention has been presented for purposes of illustration and description, but is not intended to be exhaustive or limited to the invention in the form disclosed. Many modifications and variations will be apparent to those of ordinary skill without departing from the scope and spirit of the invention. The embodiment was chosen and described in order to best explain the principles of the invention and the practical application, and to enable others of ordinary skill in the art to understand the invention for embodiments with various modifications as are suited to the particular use contemplated.

What is claimed is:

1. A composite orthosis comprising:
    an upper part configured to be aligned with a lower leg of a wearer;
    a laminate fiber-reinforced composite strut extending from the upper part; and
    a footplate connected to the strut, the footplate configured to be underneath a foot of a wearer,
        wherein the strut comprises a plurality of fiber-reinforced composite layers comprising, a first composite layer having a side edge, the first composite layer positioned and shaped to extend from the upper part and to be connected to the footplate, and a second composite layer containing reinforcing fiber, the second composite layer having a first side edge and a second side edge, the second composite layer positioned and shaped to extend from the upper part, the second composite layer having a lower end with a distal edge, the distal edge spanning the second composite layer's first side edge and the second composite layer's second side edge, the total length of the distal edge of the second composite layer being greater than the shortest distance between the first side edge and the second side edge of the second composite layer when measured at the lower end where the first side edge and the second side edge meet the distal edge, the lower end of the second composite layer including a portion not parallel to the side edge of the first layer, and the distal edge of the lower end of the second composite layer having a first portion resident in the footplate and a second portion not resident in the footplate.

2. The orthosis of claim 1 wherein the distal edge of the second composite layer has a first section and a second section that are together configured in the shape of two or more sides of an isosceles triangle.

3. The orthosis of claim 1 wherein the strut is positioned to be on one side of the ankle of the wearer only.

4. The orthosis of claim 1 wherein the strut is positioned only on the lateral side of the orthosis.

5. The orthosis of claim 1 wherein reinforcing fiber comprises one or more of carbon, glass, and aramid fibers.

6. The orthosis of claim 1 wherein one or more of the composite layers includes thermo-set or thermo-plastic.

7. The orthosis of claim 1 wherein one or more of the composite layers is taken from prepreg.

8. The orthosis of claim 1 wherein at least the first or second layer comprises woven fiber.

9. The orthosis of claim 1 wherein at least the first or second layer comprises UD fiber.

10. The orthosis of claim 1 further comprising a third layer and a fourth layer where each of the third and fourth layers are positioned and shaped to extend from the upper part, and each of the third and fourth layers have a lower end with a distal edge spanning the side edges of the second layer, the length of the distal edge of at least the third or fourth layer being greater than the distance between the side edges of the second layer, the lower end of the third or fourth layer including an apex, or defined by a plurality of connected lines or curves or defined by both a plurality of connected lines and curves.

11. The orthosis of claim 1 wherein when under a measurable static or dynamic load to the orthosis, the strut has a first load to maximum strength ratio in top third of the strut and a second load to maximum strength ratio in the bottom third of the strut, and wherein the numerical value of the quotient of the second load to maximum strength ratio over the first load to maximum strength ratio, is larger than 1.0.

12. The orthosis of claim 1 wherein the first portion of the distal edge of the second composite layer and the second portion of the distal edge of the second composite layer are connected.

13. An orthosis comprising:
a footplate; and
a strut, the strut having a top end and a bottom end, wherein,
the strut comprises a plurality of fiber reinforced layers stacked upon each other,
the bottom end of the strut is connected to the footplate, and
when the strut is under a first load, the numerical value of the quotient of the first load to maximum strength ratio determined within the bottom end of the strut over the numerical value of the first load to maximum strength ratio determined within the top end of the strut, is larger than 1.0.

14. The orthosis of claim 13 wherein
the strut comprises at least three fiber reinforced layers,
wherein each of the three layers comprises two long side edges and an end, and
wherein the end of a first layer comprises an edge positioned between the two long side edges and is longer than the distance between the two side edges.

15. The orthosis of claim 14 wherein the end of the first layer is a proximal end closer to the top end of the strut than the footplate.

16. The orthosis of claim 13 wherein when under a static or dynamic orthosis load, the strut has a first load to maximum strength ratio in the top third of the strut and a second load to maximum strength ratio in the bottom third of the strut, and wherein the numerical value of the quotient of the second load to maximum strength ratio over the first load to maximum strength ratio, is larger than 1.0.

17. The orthosis of claim 13 wherein at least one of the fiber reinforced layers comprises one or more areas of cutout material from that fiber reinforced layer.

18. The orthosis of claim 13 wherein an end of at least one of the reinforced layers has an apex, where the apex is not positioned on a centerline of the reinforcing layer, the centerline positioned between two side edges of the reinforced layer.

19. An orthosis comprising:
a laminate strut;
a lower leg attachment; and
a footplate;
the strut connecting the lower leg attachment to the footplate;
the strut comprising three layers of fiber reinforced composite,
wherein each of the three layers has two long side edges and a lower end,
wherein the lower end of a first layer has an edge that is longer than the distance between its two side edges when the distance is measured between the side edges at the lower end of the first layer,
wherein when the strut is under a static or dynamic load, the strut has a first load to maximum strength ratio in the top third of the strut and a second load to maximum strength ratio in the bottom third of the strut,
wherein the numerical value of the quotient of the second load to maximum strength ratio over the numerical value of the first load to maximum strength ratio, is larger than 1.0.

20. The orthosis of claim 19 wherein the static or dynamic load is a static load.

21. The orthosis of claim 19 wherein the static or dynamic load is a dynamic load.

22. A composite orthosis comprising:
an upper part configured to be aligned with a lower leg of a wearer;
a laminate fiber-reinforced composite strut extending from the upper part; and
a footplate connected to the strut, the footplate configured to be underneath a foot of a wearer,
wherein the strut comprises a plurality of fiber-reinforced composite layers comprising,
a first composite layer having a side edge, the first composite layer positioned and shaped to extend from the upper part and to be connected to the footplate, and
a second composite layer containing reinforcing fiber, the second composite layer having a first side edge and a second side edge,
the second composite layer positioned and shaped to extend from the upper part, the second composite layer having a lower end with a distal edge, the distal edge spanning the second composite layer's first side edge and the second composite layer's second side edge,
the total length of the distal edge of the second composite layer being greater than the shortest distance between the first side edge and the second side edge of the second composite layer when measured at the lower end where the first side edge and the second side edge meet the distal edge,
the lower end of the second composite layer including a portion not parallel to the side edge of the first layer,
the distal edge of the second composite layer having at least a portion that does not extend into the footplate, and
the distal edge of the second composite layer having at least a portion that does extend into the footplate.

* * * * *